(12) United States Patent
Kramer et al.

(10) Patent No.: US 9,429,521 B2
(45) Date of Patent: Aug. 30, 2016

(54) PLANT PHENOMETRICS SYSTEMS AND METHODS AND DEVICES RELATED THERETO

(71) Applicant: BOARD OF TRUSTEES OF MICHIGAN STATE UNIVERSITY, East Lansing, MI (US)

(72) Inventors: David Kramer, Okemos, MI (US); Jeffrey Cruz, Okemos, MI (US); Christopher Hall, East Lansing, MI (US); William Kent Kovac, East Lansing, MI (US); Robert Zegarac, Okemos, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 14/404,338

(22) PCT Filed: May 30, 2013

(86) PCT No.: PCT/US2013/043426
§ 371 (c)(1),
(2) Date: Nov. 26, 2014

(87) PCT Pub. No.: WO2013/181433
PCT Pub. Date: Dec. 5, 2013

(65) Prior Publication Data
US 2015/0204787 A1 Jul. 23, 2015

Related U.S. Application Data

(60) Provisional application No. 61/653,274, filed on May 30, 2012.

(51) Int. Cl.
*G01N 21/64* (2006.01)
*G01N 33/02* (2006.01)
(Continued)

(52) U.S. Cl.
CPC ...... *G01N 21/6486* (2013.01); *G01N 21/6408* (2013.01); *G01N 21/6456* (2013.01);
(Continued)

(58) Field of Classification Search
CPC . G01N 21/63; G01N 21/64; G01N 2021/635
USPC .............. 250/459.1, 458.1, 461.1, 461.2
See application file for complete search history.

(56) References Cited

U.S. PATENT DOCUMENTS

| 4,650,336 A | 3/1987 | Moll |
| 5,412,219 A * | 5/1995 | Chappelle .............. G01N 21/64 250/253 |

(Continued)

FOREIGN PATENT DOCUMENTS

| DE | 19910436 A1 | 10/2000 |
| WO | 2013/181433 A2 | 12/2013 |
| WO | 2013/181433 A3 | 1/2014 |

OTHER PUBLICATIONS

International Search Report and Written Opinion received for PCT Patent Application No. PCT/US2013/043426, mailed on Nov. 12, 2013, 8 pages.

(Continued)

*Primary Examiner* — David Porta
*Assistant Examiner* — Djura Malevic

(57) ABSTRACT

Chlorophyll fluorescence may be studied in response to a variety of environmental cues or conditions by growing phototrophic organisms under actinic illumination. Such illumination may be punctuated or disrupted to gain information about the photosynthetic properties or performance of the phototrophic organism. Instruments or devices for carrying out the method are also described.

27 Claims, 9 Drawing Sheets
(6 of 9 Drawing Sheet(s) Filed in Color)

(51) Int. Cl.
*G01N 21/63* (2006.01)
*G01N 21/84* (2006.01)

(52) U.S. Cl.
CPC ....... *G01N33/025* (2013.01); *G01N 2021/635* (2013.01); *G01N 2021/8466* (2013.01); *G01N 2201/0221* (2013.01); *G01N 2201/0627* (2013.01); *G01N 2201/0628* (2013.01)

(56) References Cited

U.S. PATENT DOCUMENTS

| | | | |
|---|---|---|---|
| 6,121,053 | A | 9/2000 | Kolber et al. |
| 6,563,122 | B1 | 5/2003 | Lüdeker et al. |
| 7,214,947 | B2 * | 5/2007 | Bueno et al. ............. 250/370.11 |
| 7,857,993 | B2 * | 12/2010 | Dai et al. ................. 252/301.17 |
| 8,302,346 | B2 * | 11/2012 | Hunt ....................... A01G 7/045 47/1.3 |
| 8,796,631 | B2 * | 8/2014 | Penumadu et al. ........... 250/362 |
| 2001/0030742 | A1 | 10/2001 | Kramer et al. |
| 2005/0239044 | A1 * | 10/2005 | Seibert .................... C12Q 1/02 435/4 |
| 2006/0273258 | A1 * | 12/2006 | Kastalsky et al. ....... 250/370.11 |
| 2007/0085010 | A1 * | 4/2007 | Letant et al. ............. 250/361 R |
| 2008/0128624 | A1 * | 6/2008 | Cooke et al. ............. 250/361 R |
| 2008/0237470 | A1 * | 10/2008 | Loureiro et al. ......... 250/361 R |
| 2010/0270462 | A1 * | 10/2010 | Nelson et al. ............. 250/252.1 |
| 2011/0091945 | A1 * | 4/2011 | Das ......................... C12N 1/38 435/134 |
| 2011/0179706 | A1 | 7/2011 | Hunt et al. |
| 2012/0310540 | A1 * | 12/2012 | McDermitt ........ G01N 21/6486 702/19 |
| 2013/0256561 | A1 * | 10/2013 | Greenbaum ....... G01N 21/6486 250/451.1 |

OTHER PUBLICATIONS

International Preliminary Report on Patentability received for PCT Patent application No. PCT/US2013/043426, mailed on Dec. 11, 2014, 7 pages.
Office Action received for Canadian Patent Application No. 2,874,853, mailed on Dec. 30, 2014, 4 pages.
Notice of Allowance Received for Canadian Patent Application No. 2,874,853, mailed on Apr. 30, 2015, 3 pages.
Dornbusch et al., "Measuring the Diurnal Pattern of Leaf Hyponasty and Growth in Arabidopsis—A Novel Phenotyping Approach using Laser Scanning", Functional Plant Biology, vol. 39, No. 8, Aug. 2012, pp. 860-869.
Reuzeau et al., "Traitmille: A Functional Genomics Platform for the Phenotypic Analysis of Cereals", Plant Genetic Resources, vol. 4, No. 1, 2006, pp. 20-24.
"Extended EP Search Report Received for EP Patent Application 13796653.7", mailed on Nov. 11, 2015, 11 pages.

* cited by examiner

PLANT PHENOMETRICS SYSTEMS AND METHODS AND DEVICES RELATED THERETO

RELATED APPLICATIONS

This application is a U.S. National Stage Filing under 35 U.S.C. 371 from International Application No. PCT/US2013/043426, having an International Filing Date of May 30, 2013 and published in English as WO/2013/181433 on Dec. 5, 2013, which claims the benefit under 35 U.S.C. 119(e) of U.S. Provisional Application No. 61/653,274, filed on May 30, 2012, which applications and publications are hereby incorporated by reference in their entireties.

STATEMENT OF GOVERNMENT RIGHTS

This invention was made with government support under DE-FG02-91ER20021 awarded by the U.S. Department of Energy. The government has certain rights in the invention.

BACKGROUND

Photosynthesis is a complex process that can be potentially dangerous to the organism under many circumstances. For example, energy captured in the form of photons can exceed the rate at which the energy can be used, resulting in reactive oxygen species (ROS) production and cell damage. Many systems or mechanisms have evolved to cope with this challenge, some that are fast responding, such as photo protection via the qE response, and others that are slower responding, such as the induction of genes encoding proteins that can detoxify ROS.

What is not known is how these different mechanisms are integrated and the degree to which given mechanisms take precedence under specific environmental conditions. For example, the same mechanisms may be activated in the same series when plants at low temperature are subjected to a change in light intensity as those that occur when plants that are experiencing drought and also experiencing a change in light intensity. Therefore, understanding how real-time, dynamically fluctuating systems affect plant status (e.g. photosynthetic productivity, efficiency, growth or the like) are useful for improving a plant's response to the environmental conditions or cues (e.g. abiotic or biotic).

Moreover, rapid fluctuations in certain environmental conditions can require the action of certain protective mechanisms that are not required when the environmental condition is held constant. Plants and other organisms have evolved to cope with unpredictable, dynamically fluctuating environments or conditions, yet study or evaluation of these organisms is conducted largely under constant (laboratory) conditions. While this experimental design is extremely powerful, it is unlikely to detect novel biochemical and regulatory mechanisms that have valuable roles in nature. For example, disrupting key photosynthetic responses often have little effect on growth or photosynthesis in the laboratory, but are strongly deleterious in the field.

SUMMARY

To accurately understand an organism's response to its dynamically fluctuating environment requires systems and methods that can reproduce such natural environments. Information obtained from such systems and methods may reveal an organism's response to these environments and aid in improving the organism's productivity and robustness to the particular environment. Such systems and methods may also reveal otherwise undetectable properties or differences in an organism compared to systems and methods that provide static, constant environments.

In one embodiment, disclosed is a method of measuring a photosynthetic parameter comprising:
  (a) illuminating a phototrophic organism with actinic illumination;
  (b) switching off the actinic illumination;
  (c) pulsing the phototrophic organism with a measuring light within a period where the actinic illumination is switched off;
  (d) collecting chlorophyll fluorescence data within the within a period where the actinic illumination is switched off; and
  (e) determining a photosynthetic parameter from the fluorescence data.

In another embodiment is a system for measuring a photosynthetic parameter comprising:
  an actinic light source provides a wavelength from about 380 to about 750 nm;
  a measuring light source;
  a sensor for capturing chlorophyll fluorescent data; and
  one or more processing units that controls the actinic light source, measuring light source and receives and analyzes the fluorescent data.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

In the following detailed description, embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of the various embodiments is defined only by the appended claims.

Plants must operate under unpredictable, often rapidly fluctuating environmental conditions (e.g. temperature, drought, light, humidity, wind and the like). For example, cloud cover and leaf movement can produce order of magnitude changes in irradiance on the seconds time scale. These changes are superimposed on perturbations in temperature, humidity, wind and other such environmental perturbations. Accordingly, photosynthesis is highly regulated. Understanding a plant's response to these changing environments may allow for improving the robustness of the plant's energy storage, and efficiency, which has immediate implications for the sustainability of food and fuel needs.

Described here is a system and method that allows for directly, continuously and non-invasively assessing the rapid and long-term responses of large number of plants under dynamic, fluctuating environmental conditions. Chlorophyll fluorescence is a useful probe of photosynthetic processes. Understanding chlorophyll fluorescence provides information on other photosynthetic properties or parameters including photosystem II, photochemical efficiency, non-photochemical quenching, photo inhibition, NDH activity, chloroplast movements, stomatal conductance and the like.

To evaluate the test organism under dynamic environmental conditions, various inputs that simulate such environmental conditions are contemplated. For example, the conditions that change rapidly and that are most relevant to photosynthesis include light intensity, light quality, light duration, temperature and carbon dioxide levels.

Figure 1:
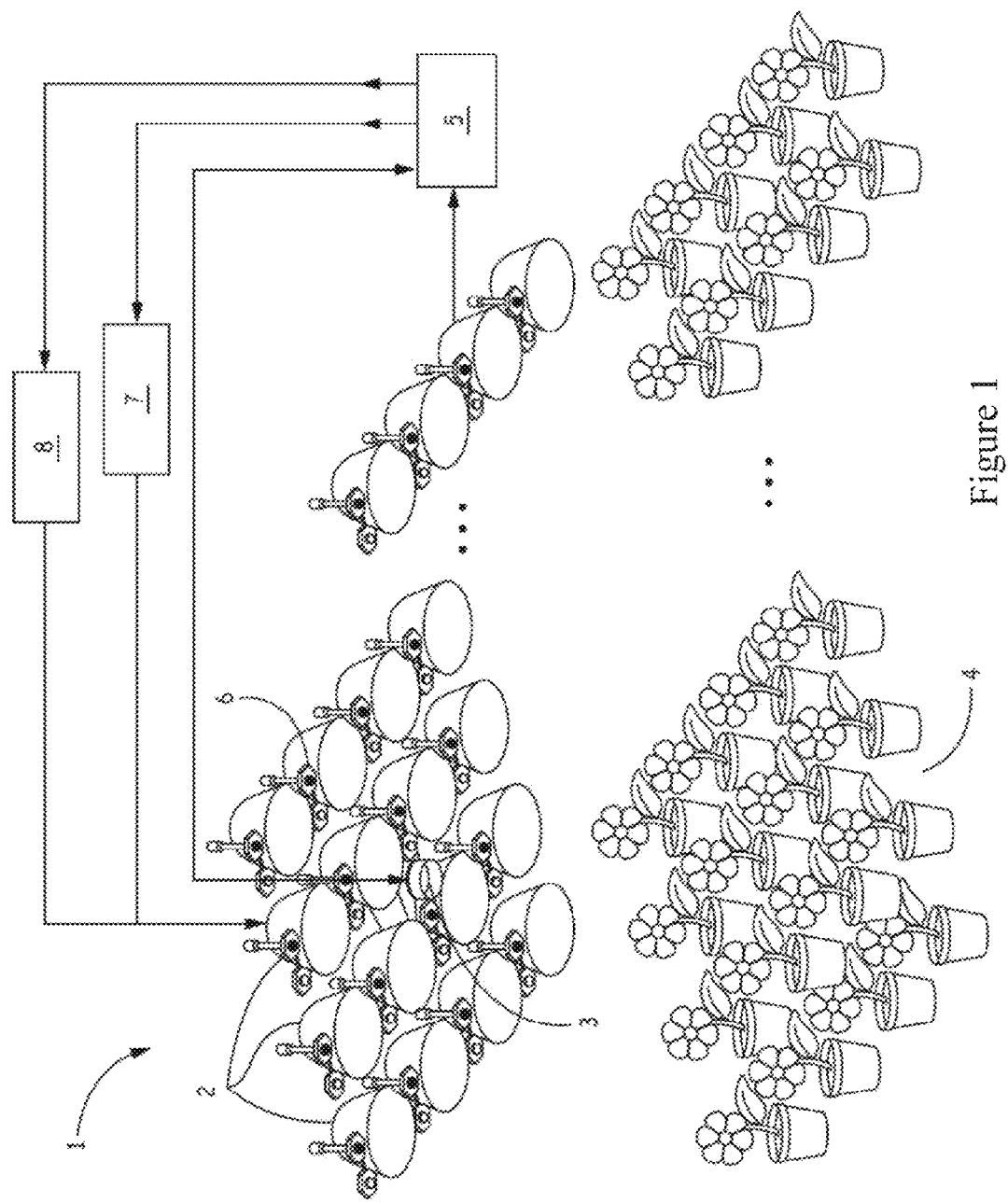
FIG. 1 is a perspective view of the disclosed system according to an embodiment.

In one embodiment and as depicted in FIG. 1, a system is provided that can simulate specific, dynamic field conditions, capture and process an organism's response to these conditions. The system 1 includes an input that generates specific environmental cues or conditions 2, and includes sensors 3 appropriate for monitoring the response of the test organism 4 to the environmental cue 2. The information or data obtained through the sensors 3 can then be captured and transmitted to a processing unit 5 (e.g. a computer or any such system) that can process, analyze and store such data.

Figure 2:
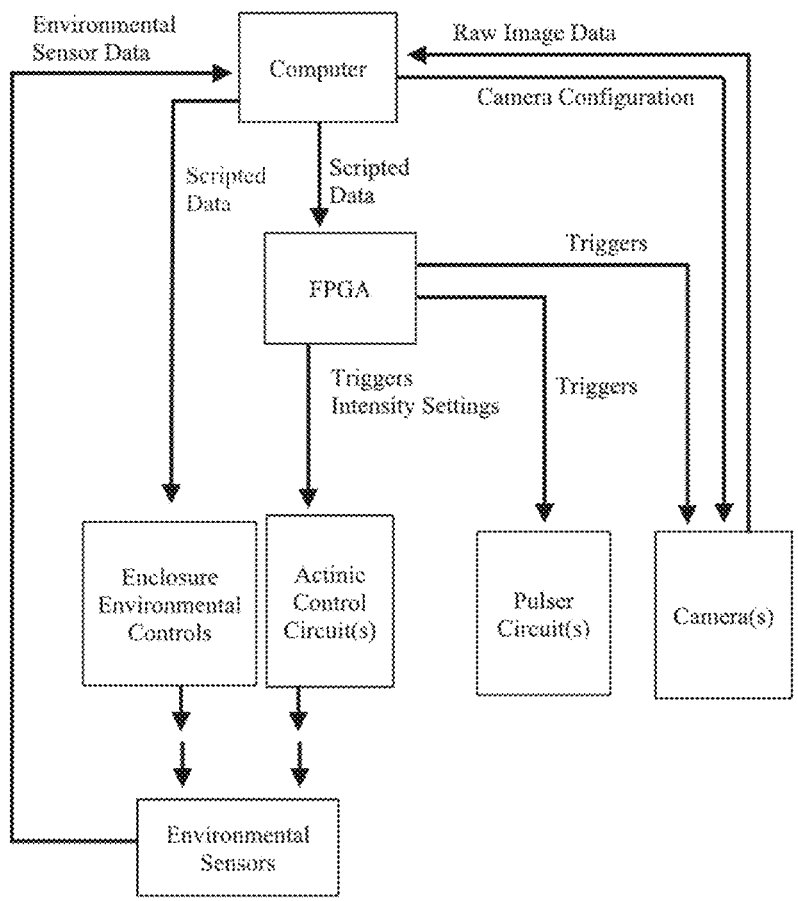
FIG. 2 is a schematic for lighting and imaging of the disclosed system according to an embodiment.

One or more processing units may be contemplated depending on the processors used. As shown in FIG. 1, the generator of environmental cues or conditions 2 may be an LED light source. An additional light source referred to as a measuring light (pulse/probe) source 6 is also included. As shown in FIG. 1, power source 7 may be used to provide the appropriate light intensities and functioning for the light sources. FIG. 2 further provides information about the lighting and imaging.

The light source used desirably should provide various wavelengths or combination of wavelengths. The light source should also be configured to allow dynamic control over light intensity, duration and quality. In other words, the light source desirably should allow reproducing natural light intensity fluctuations that occurs under field conditions. To this end, the system is adapted to accept any number of lights, in any combination, allowing the light spectral quality, quantity and duration to be dynamically adjusted. This capability, for example, assists in simulating the light quality changes that occur at dusk and dawn or the cloud passage, sun flecks in plant canopies or other such like situations.

Illumination sources desirably are capable of providing light that simulates sunlight or the full solar spectrum and that can be rapidly altered. Desirably, the light is such that it provides actinic illumination. By "actinic" is meant that the light may be suitable for the natural growth of the organism, including white light that mimics solar spectrum and that may activate the photosynthetic apparatus as well as biological light sensors such as phytochromes, cryptochromes and green light receptors that affect the growth, development and other behaviors (e.g. chloroplast movements) of the organisms.

Light sources may include, for example, halogen lamps, one or more light emitting diodes (LEDs), lasers, specially designed xenon lamps and the like, and a combinations thereof.

Compared to fluorescent and incandescent lighting, LEDs with appropriate optics can deliver higher light intensities at greater distances with more precise control over light intensity, and more rapid and precise switching (on and off). This level of control allows capturing a fluorescence image generated from a pulsed light of fixed duration and intensity during a brief interval in which actinic illumination is switched off or shuttered.

The LED illumination system can include a light source that includes one or more LED or Organic Light-Emitting Diode (OLED), where the LED(s) can emit light at different wavelengths. Desirably, white LED lighting may be used as the actinic light as these lights spectrally, more closely resemble natural lighting conditions that are used for growing plants, compared to individual or combinations of LEDs of discrete wavelengths. Exemplary white LEDs desirably provide a wavelength of about 380 nm to about 750 nm or about 420 nm to about 730 nm White LEDs with a colored temperature of between 5000k to about 7000K may also be used. For example commercially available white LEDs include Bridgelux 50 watt white LED arrays or Cree 10 watt white LEDs. In other embodiments, light approximating solar emission can be simulated by combining light from a series of LEDs with a range of emission wavelength that span the solar spectrum. The overall spectrum may be tuned by changing the emission from each type of LED by adjusting its electrical current.

A measuring light source (e.g. probe or pulsed light) used to excite chlorophyll fluorescence may include white or monochromatic light such as a red, blue or green LEDs or any light within the visible range. Such measuring light may be provided by LEDs (e.g. red LEDs, blue LEDs or green LEDs).

The light source may further include compound parabolic concentrators to collimate the light. Such a configuration better simulates sunlight and allows higher light intensities to be reached at greater distances. The light source for growth may be configured or adapted to provide continuous white light intensities in excess of full sunlight (e.g. fluencies in excess of about 2,500 micro moles photons $m^{-2}\ s^{-1}$) and in excess of about 20,000 micro moles photons $m^{-2}\ s^{-1}$, for example, 10× sunlight for photosynthetic measurements, at a distance of about 0.5 meters or greater from the light source. For example, the light intensities may be provided at distances of greater than 1 meter, greater than 1.5 meters, greater than 2 meters or greater than 2.5 meters. Power supplies that may support light intensities in excess of about 2,500 micro moles photons $m^{-2}\ s^{-1}$ are desired. For example, power to the LEDs may be provided by DC power supplies or conventional batteries.

The light may also desirably be rapidly adjusted. For example, light may be adjusted by regulating the electrical current passing through an LED. This may be accomplished by computer control via an electrical circuit that regulates the conductive status of a transistor or similar device. For example, and as illustrated in FIG. 2, using a programmable high speed timing card or similar device including an preconfigured Fully Programmable Gate Array (FPGA) or microcontroller can be used to send signals for setting intensity by a control circuit (such as a current limited feedback control circuit) and for rapidly switching actinic light off and on by a rapid gating circuit (such as a rapid switch circuit using MOSFETs and MOSFET controllers).

Light quality can be controlled by supplemental illumination with separate LED arrays of various colors, including ultraviolet, visible and near infrared light.

Depending on the desired environmental condition or the parameter to be evaluated, appropriate sensors may be used. For example, if light is the environmental cue, various sensors or imagers are contemplated. Exemplary sensors include, but are not limited to, cameras such as video cameras or high time resolution computer controlled video cameras, or cameras with charge coupled devices (CCD), complementary metal-oxide semiconductor (CMOS) cameras or silicon sensor arrays. These cameras or sensor arrays may be further equipped with optical filters to collect chlorophyll fluorescence images. For example, the cameras may include filters for far red or near infrared (680 to 730 nm) where chlorophyll fluorescence occurs. The sensors include one or more sensors and may be arranged in any configuration to allow for imaging any area configuration.

The sensors may be part of the light source such as, for example, an integrated diode emitter array (IDEA). Integration of multiple sensors (e.g., cameras) into the lighting system allow substantially simultaneous imaging of the entire growing area minimizing data collection time and external stress on plant groups by eliminating the need to move the plants individually from the enclosure to an imaging device, although such practice remains a viable option.

The system may also be equipped for thermal imaging (e.g. for terahertz (THz) imaging) and spectroscopy. In such embodiments, non-ionizing radiation is provided to the plant parts such as leaves, flowers and fruits to non-invasively monitor the plant. For example, using THz wavelengths, which are sufficiently short allow for imaging of e.g. vein or stems. The THz non-ionizing radiation may also be able to be absorbed by water, making it a useful tool to detect plant moisture content in parts of a plant such as in a leaf. THz imaging may be used alone or in combination with chlorophyll florescence imaging or other parameters being studied. In such cases, the relationship of water movement and photosynthesis may be evaluated.

In some embodiments, the system is designed to accommodate a myriad of sensors. For example, the sensors may include photodetectors, electrodes, pH electrodes, gas detectors, gas or nutrient sampling devices. Other sensors include, for example, the sensor(s) for detection of temperature, light intensity, light penetration, aeration, $CO_2$ concentration or flow, oxygen concentration, photosynthesis, and combinations thereof.

The captured data may be transferred either wirelessly or through a wire hardwired to a processing unit. The processing unit may be remotely located or embedded in a handheld, portable system. A microprocessor or microcontroller may be connected to the system or cues to control, monitor or vary any number of environmental inputs or cues the test organism is exposed to, and to measure any number of parameters of the exposed test organism and provide a suitable digital output.

In one embodiment, the system includes a processor for storage and or modulation of information received from the sensors. The system can include software executable on a suitable computer or series of computers connected to the sensors and allows continuous control of all parameters and collection of data and integration of photosynthetic parameters over diurnal cycles or continuous growth.

In one embodiment, environmental data can be "played back" via the appropriate sensor thus simulating previously recorded real environmental data.

The captured data (e.g. chlorophyll fluorescence measurements, spectral data, and other parameters or combinations thereof) may be further analyzed. For example, independent component analysis (ICA) techniques may be used for decomposing mixed transient signals into unique source components. In other embodiments, multi-sensor data fusion tools may be used. The algorithms provided are capable of exploiting sensor-generated information that may be redundant and complimentary to enhance the resulting image. In yet other embodiments, images from multi-band cameras may be fused to generate more accurate and enhanced images for analysis. It will be understood that conventional tools to mine or extract information from the obtained data may also be used.

The system may be adapted to any suitable enclosures. Exemplary enclosures may include growth chambers, green houses, portions of green houses that are configured to include the desired environmental inputs and the appropriate sensors. The enclosures may be further configured such that organisms under study are exposed to only the environmental condition under study (e.g. light) and not any stray or non-tested environmental source or cue.

In one embodiment, the enclosure may be sufficiently large to substantially mimic (replicate or reproduce) field conditions, or compact to be useful for high throughput analysis. The term "high-throughput analysis" refers to testing in which multiple variables (e.g., environmental conditions or cues related to productivity) are analyzed substantially simultaneously. "High-throughput analysis" is in contrast to "traditional analysis" in which separate experiments are conducted in which only a single variable can be analyzed per experiment. Traditional analysis also requires more time as compared to high-throughput analysis, with the time differential between traditional and high-throughput related to the number of parameters being analyzed.

In one embodiment, for high-throughput parallel growth and phenotypic analyses, a variety of plant strains under controlled, but variable, growth conditions may be evaluated for a variety of phenotypic parameters. The disclosed system may also be modular, allowing modules to be added or removed at any time. The disclosed system may further be portable or handheld.

The enclosure may also be adapted to provide radiant heat, to simulate the effects of direct sunlight, and can be controlled, for example, by optional quartz heating elements. The chambers rapidly control temperature, e.g. from $-20°$ C. to $+50°$ C., with a rate of change of greater than $10°$ C./hour, relative humidity, e.g. from 30 to 90%, wind (e.g. via optional fan units), e.g. from 2 to 30 kph, and the introduction of gases such as $CO_2$, ozone, oxygen, CO allowing for simulation of field fluctuations in environmental parameters.

A variety of parameters from a variety of organisms may be studied or evaluated using the disclosed system and method. In one embodiment, any phototrophic organism may be studied. As used in this application, "phototrophic organisms" mean an organism that obtains energy from sunlight for the synthesis of organic compounds and include plants, algae and cyanobacteria.

Plants may include monocots and dicots and are not limited to species such as *Arabidopsis*, tobacco, soybean, corn, wheat, rice, cotton and various ecotypes and the like. The plant species further may be modified by genetic engineering or traditional breeding and also includes plant libraries that have been mutagenized (e.g. T-DNA or chemically). The plants are not limited to any particular development stage and may include early stage plant development. Plants may also be whole plants, plant parts (e.g. stem, leaf), plant preparations (e.g. thylakoid or other chloroplast preparation), tissue cultures (e.g. calli or explants), and cell suspension cultures (e.g. single or lumped).

As noted above, measuring chlorophyll fluorescence provides information on other photosynthetic properties or parameters. Shown below is a table of the parameters measured and the additional information that may be obtained by the disclosed system and method.

TABLE 1

| Parameters Measures | Measurement | Reflects Measures | Sensor |
|---|---|---|---|
| $\phi_{II}$ and $F_V/F_M$ | Photosystem II photochemical efficiency | Efficiency of photosystem II photochemistry | Chlorophyll fluorescence |
| LEF | Linear electron flow, calculated from $\phi_{II}$ and incident PAR | Rate of photosystem II electron transfer | Chlorophyll fluorescence |
| NPQ | Non-photochemical quenching | The rate of dissipation of adsorbed light energy as heat reflects the fraction of adsorbed light that is "wasted" as heat. | Chlorophyll fluorescence |
| qE and qE$_{SV}$ | Rapidly reversible NPQ component | Engagement of photoprotective NPQ responses | Chlorophyll fluorescence |
| qI | Long-lived NPQ | Oxidative photodamage to and repair of photosystem II | Chlorophyll fluorescence |
| qP, qL | Redox status of photosystem II | Backup of electrons in photosystem II resulting from imbalances in light input, downstream sink capacity and photoprotection | Chlorophyll fluorescence |
| $q_{pi}$ | Post-illumination recovery of fluorescence | Activation of cyclic electron transfer via the NDH complex, engaged under environmental stresses | Chlorophyll fluorescence |
| $A_L$ | Leaf/plant surface area | Leaf area, above-ground biomass and growth | Reflectance |
| $dA_L/dt$ | Change in surface area over time | Growth rate | Reflectance |
| LEF$_{total}$ | Total plant LEF, calculated from LEF and $A_L$ | Total LEF across the plant | Reflectance and Fluorescence |
| $R_R$ | Relative reflectance and adsorptivity of the leaf | Reflects chlorophyll content and chloroplast orientation | Reflectance |
| $dR_R/dt$ | Change in red reflectance as a function of time | Light-induced red reflectance changes monitoring chloroplast movements, useful for certain modes of photoprotection | Reflectance |
| $T_L$ and $T_S$ | Leaf and soil temperatures | Transpiration rate, stomatal aperture and dynamics thereof | Thermal imaging |

Desirably, one or all photosynthetic parameters may be evaluated as any one of the above parameters may be affected by any set of chosen environmental conditions.

In addition to the light intensity, light duration and spectral wavelength and quality, the temperature, gases, water or nutrient content may be used to evaluate the effect on chlorophyll fluorescence. It should be understood that depending on the parameter to be measured and evaluated, the enclosures with the appropriate environmental cue and sensor may be configured accordingly. Various genes, gene sets and profiles (e.g. regulatory genes and the like) ROS production, metabolites, pigments, seed production, biomass and the like may also be evaluated.

The chlorophyll fluorescence profiles or any of the data generated under the varying environments for the test phototrophic organisms may be used to generate databases or data may be compared to other phototrophic organisms and also may be used to generate photosynthetic "signatures".

In some embodiments, a white LED lighting system is used to provide actinic light (e.g. photosynthetic active) and measure (probe or pulsed light) changes in chlorophyll fluorescence.

Figure 3:
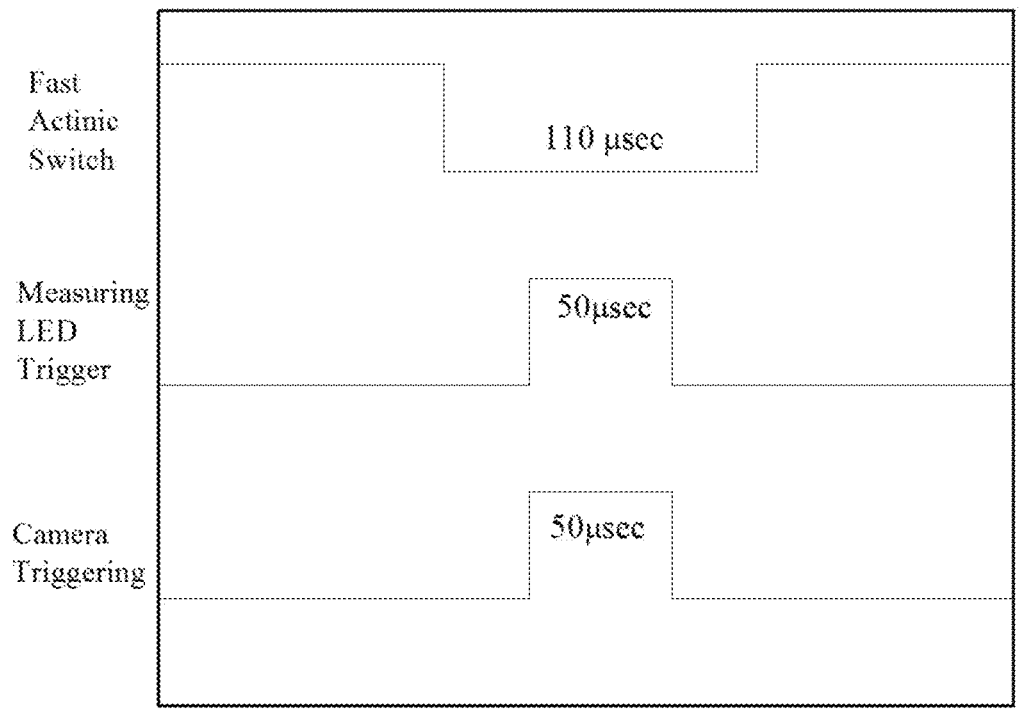
FIG. 3 is a schematic diagram of light application according to an embodiment.

In one embodiment, and referring to FIG. 3, chlorophyll fluorescence data may be collected by switching off or shuttering actinic light (e.g. about 100 to about 120 microseconds) on the test organism. During this period when the actinic illumination is shuttered or switched off, the test organism is exposed to a flash or pulse of a measuring light of one or more desired wavelengths or intensities to excite fluorescence. The duration of the measuring flash or pulse is brief, e.g. from about 1 to about 50 microseconds. The duration of the period when actinic illumination is shuttered, may be long enough to capture a high resolution image (e.g. about 5 to about 50 microseconds), but short enough to minimize perturbations to photosynthesis (e.g. about 120 microseconds or less). This "punctuated illumination" may allow the use of white (or other emission wavelength) light illumination for both growth and excitation of photosynthesis. For example, plants may be both grown and measured in the same environment, continuously and provides imaging of both rapid (sub-second) and long-term (days to months). At such short times between switching off illumination and application of the measuring flash or pulse, the photosynthetic system does not substantially relax, so that the flash or pulse measures the properties of the system as it was prior to the dark interval. Such a method provides minimizing of spectral contamination of chlorophyll fluorescence in the near infra red by actinic illumination; prevents blinding of the camera by the actinic saturating flash or measuring pulse or flash without changing camera gain or image capture duration and allows using of white light (e.g. white LED), permitting continuous measurement and long term (days to weeks) experiments which were not possible in traditional chlorophyll fluorescence imaging systems which use monochromatic light for actinic illumination.

In the various embodiments, fluorescence images can be captured by a high resolution CCD camera outfitted with a filter specific for chlorophyll fluorescence (far red to near infrared; 680 to 730 nm). Fluorescence produced from a measuring pulse by a test organism under actinic illumination is obtained by subtracting a background image from one with a measuring pulse.

In one embodiment, a first wavelength can be used to provide actinic light and a second wavelength can be used to act as probing light. For example, long term imaging exclusively under red actinic light may be used to simulate $CO_2$ stress, since blue light (and not red) is an inducer of stomatal opening. Differential excitation by blue and red light can be used to determine the effects of chloroplast movements because these are triggered by blue light. Chloroplast movement provides photoprotection to plants by redistributing PSII damage within leaves. In another embodiment, the lights provide short (e.g. about 0.5 to about 1 second) white light pulses in excess of 10-fold full sunlight to saturate photochemistry. In other embodiments the frequency of the measuring pulses may vary. For example, the measuring pulses may be as series of measuring pulses form about 1 to about 100 measuring pulses.

Precision control over the actinic illumination allows simulating fluctuations in light intensity as they occur in nature, which may more effectively reveal the effect of mutating specific photosynthetic and related genes/mechanisms to plant survival and productivity than the static lighting conditions in plant growth chambers.

The disclosed system and method may be used in a number of applications, including, but not limited to testing various phototrophic organism strains, mutations, or phototrophic organism subjected to different growth conditions, temperature, $CO_2$ levels, $O_2$ levels, intensity, concentration of gas, light intensity, light quality, light duration, temporal variations in temperature, injection of chemicals and nutrients, and the like or combinations thereof for the purposes of basic research or optimizing photosynthesis, and the like. The system and method may be also be used for identifying varieties and mutants and optimizing conditions for efficient and effective photosynthesis (e.g. $CO_2$ sequestration, for photosynthetic $CO_2$ scrubbing systems and the like).

For example, the disclosed system and method may be used to determine, select or characterize different phototrophic strains, mutations or other genotypically diverse populations particular to photosynthetic phenotypes.

The various embodiments will be further described by reference to the following examples, which are offered to further illustrate various embodiments of the present invention. It should be understood, however, that many variations and modifications may be made while remaining within the scope of the present invention.

EXAMPLE 1

Short Term Response and Long Term Adaptation to Fluctuating Light Intensity

Figure 4:
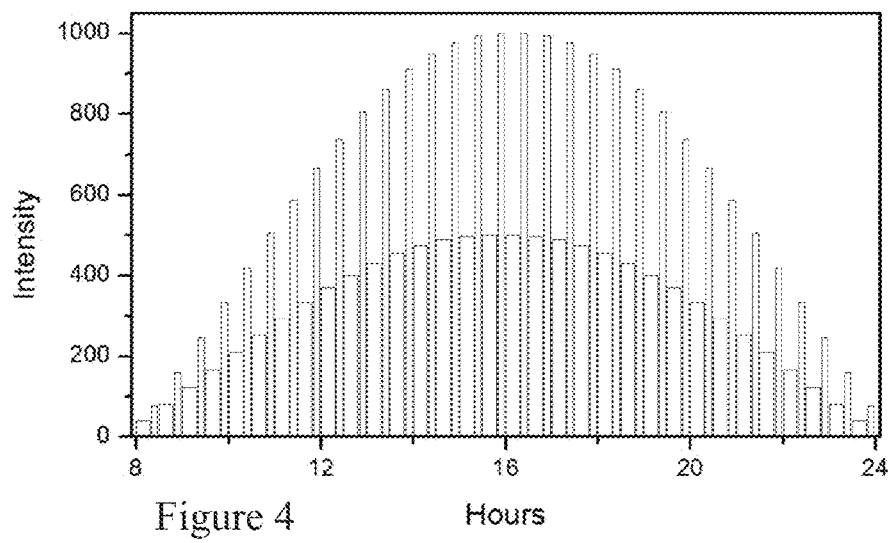
FIG. 4 shows the light intensity profile ($\mu$mol photons $m^{-2} s^{-1}$) for 16 hours of daylight according to various embodiments.

Wild type (col-0) and mutant (cfq) *Arabidopsis thaliana* seeds were grown on soil at 20° C. and 50% relative humidity. For the first 10 days, the plants were grown at constant light intensity (100 µmol photons m$^{-2}$ s$^{-1}$) with a 16:8 day:night cycle. The constant light was provided by standard fluorescent lights. After 10 days, the plants were transferred to a chamber for growth under fluctuating light. The fluctuating light was provided by an array white 50W Bridgelux (BXRA-56C5300) LEDs outfitted with collimating optics (LEDIL Britney M reflector). While the plants were grown under a 16:8 day:night cycle, the light portion of the day:night cycle was fluctuated. As shown in FIG. 4, a fluctuating light intensity profile was patterned on a sinusoidal curve for a 24 hour day. A fluctuating light interval consisted of 30 minutes. This 30 minute light interval further consisted of 18 minutes of standard illumination and 2 minutes of darkness, followed by 8 minutes of fluctuating light and 2 minutes of darkness. The standard daylight intensity was a maximum of 500 µmol photons m$^{-2}$ s$^{-1}$ and the fluctuating daylight intensity was 1000 µmol photons m$^{-2}$ s$^{-1}$.

Chlorophyll fluorescence images were collected before the beginning of each daylight cycle ($F_0$, $F_M$, in the absence or presence of saturating actinic light, respectively) as well as immediately before ($F_s$, $F_{M'}$, in the absence or presence of saturating actinic light, respectively) and at the end of each 2 minute dark period ($F_{M''}$, in presence of saturating actinic light). Images of the quantum yield of photosynthesis at Photosystem II ($\Phi_{II}$), Non-photochemical quenching (NPQ), energy dependent quenching ($q_E$) and inhibitory quenching ($q_I$) were calculated as described in (Baker and Oxborough, Springer, Netherlands, pp. 62-82, 2004). Plants were monitored for 15 days under the fluctuating light protocol.

Figure 5A:
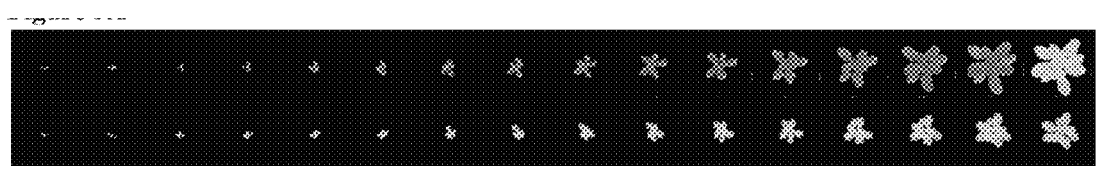
FIG. 5A shows images of $\Phi II$ collected at the end of each day for col-0 and cfq according to various embodiments.
Figure 5B:
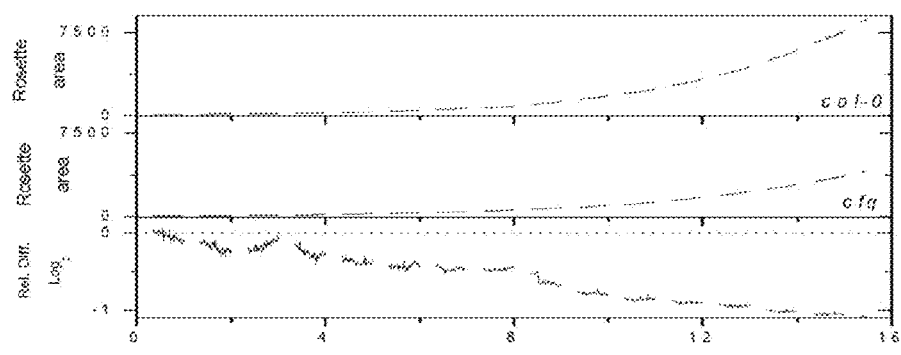
FIG. 5B shows rosette areas plotted as a function of time over a 15 day period. The relative difference between mutant and wild type was expressed as the logarithm (base 2) of cfq growth over col-0 growth according to various embodiments.

Cfq harbors a mutation on the gamma subunit of the ATP synthase. The mutant performed well under standard laboratory growth conditions (constant light, temperature, humidity), out growing wild type plants. But under fluctuating light cfq grows more slowly than the wild type control (FIG. 5A). A more quantitative estimate for growth (rosette area as shown in FIG. 5B) shows that the mutant is roughly half the size of the control plant by the end of the experiment.

Figure 6:
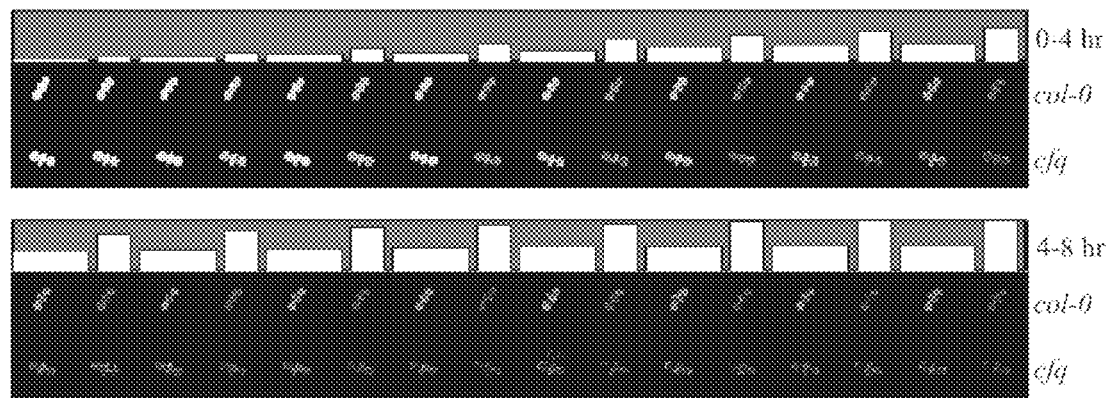
FIG. 6 shows images of $\Phi II$ collected for col-0 (upper rows) and cfq during the first 8 hours of the experiment with brighter images indicating higher values according to various embodiments. Images are lined up with bar graphs depicting the corresponding light intensities (from 0 to 1000 $\mu$mol photons $m^{-2} s^{-1}$).
Figure 7:
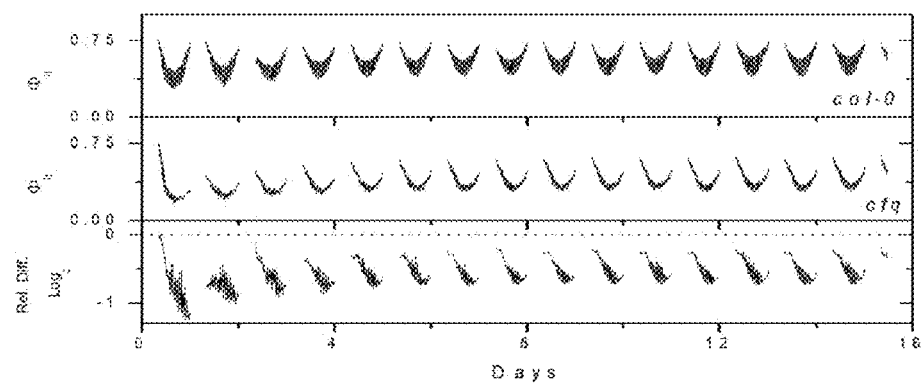
FIG. 7 shows the averaged $\Phi II$ values for col-0 and cfq over the course of 15 days under fluctuating light according to various embodiments. The relative difference between $\Phi II$ values for mutant and wild type is expressed as the logarithm (base 2) of cfq over col-0.

The slower growth rate of the mutant correlates well with diminished photosynthetic efficiency compared to the wild type. An image series from the first 8 hours of the experiment (FIG. 6) as well as plots of the average $\Phi_{II}$ values collected over 15 days (FIG. 7) show that in contrast to wild type, $\Phi_{II}$ values for cfq do not dynamically adjust to changes in light intensity. Moreover, where daily electron transfer efficiency in col-0 is transiently affected and recovers as the plants adjust, the efficiency of cfq is continuously repressed or unable to recover under fluctuating light.

Figure 8A:
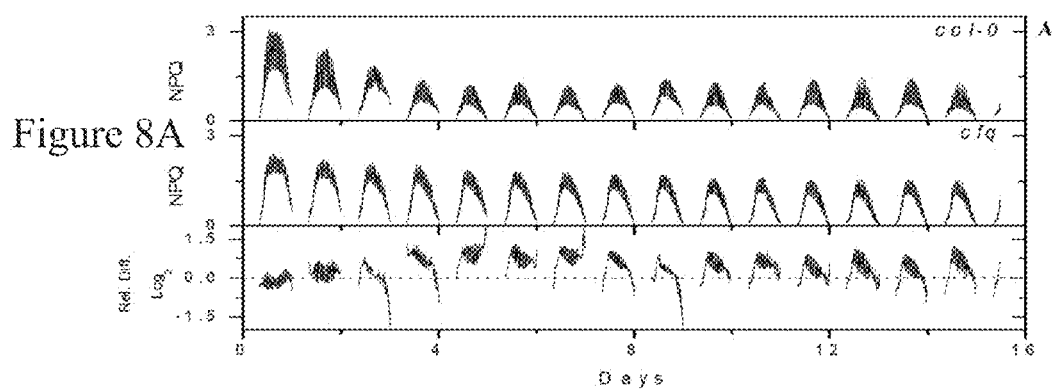
FIG. 8 shows averaged photoprotective quenching (A: NPQ, B: qE and C: qI) values for col-0 and cfq over the course of 15 days under fluctuating light according to various embodiments. The relative difference between values for mutant and wild type is expressed as the logarithm (base 2) of cfq over col-0.
Figure 8B:
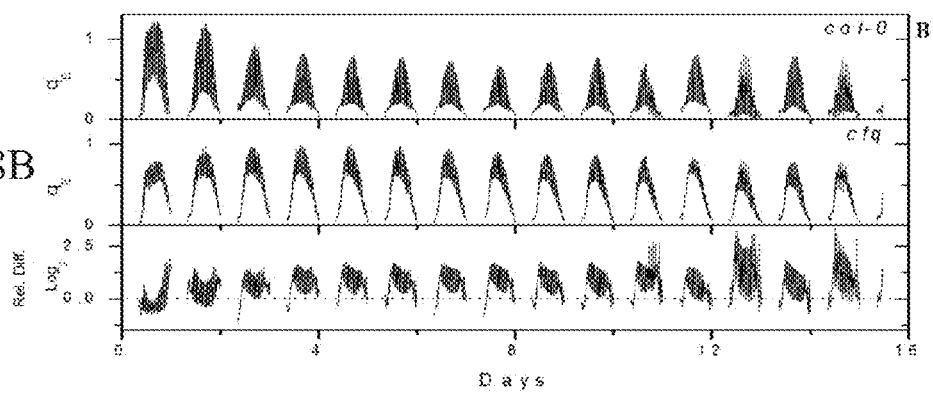
Figure 8C:
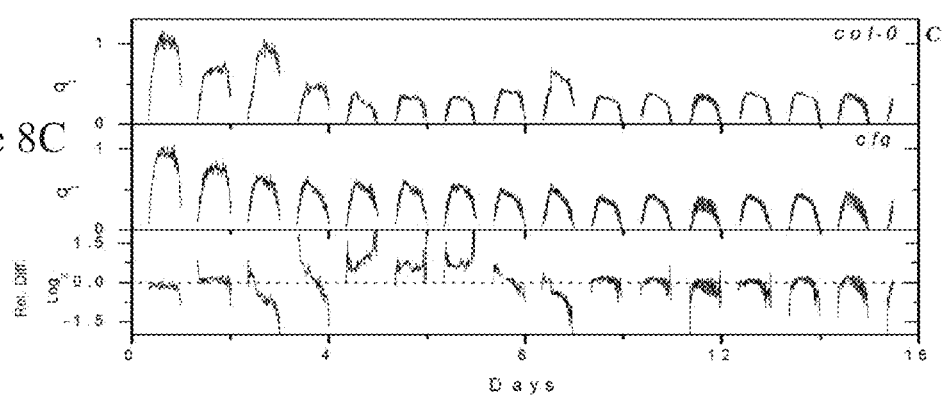
Figure 9:
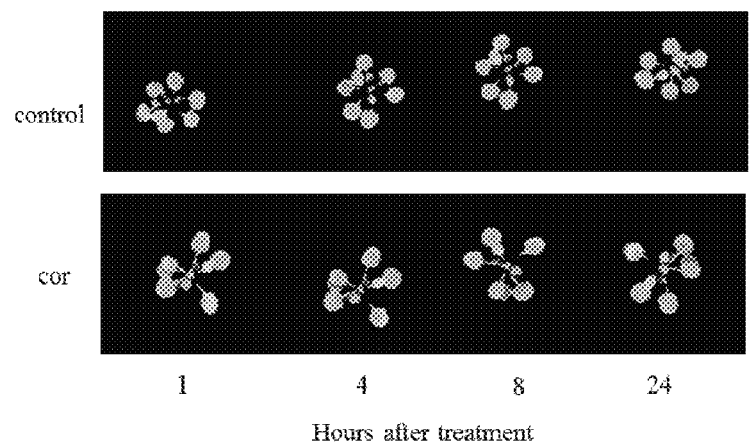
FIG. 9 shows images of ΦII generated from an imager that uses red actinic light for untreated (control) and coronatine-treated (cor) plants on the day of (1, 4 and 8 hours) and day after (24 hours) treatment according to various embodiments. Darker (blue) areas correlate with lower ΦII values.

During the first day in the fluctuating light, the extent and dynamic range NPQ and $q_E$ in response to high intensity fluctuations was limited in the mutant (FIG. 8A, B), which points towards insufficient proton motive force pmf and/or $q_E$ components to augment the $q_E$ response. In addition, the comparable levels of photoinhibition ($q_I$) between cfq and col-0 (FIG. 8C) suggest other factors limit photosynthetic efficiency, likely 'over-reduction' of the electron transfer chain.

With continued growth under fluctuating light, photoprotective quenching in col-0 decreases as it adapts. In contrast the extent and dynamic range of $q_E$ (FIG. 5B) does not appear to change significantly from day to day in cfq, and on most days $q_I$ more rapidly recovers than in col-0 towards the end of the day (FIG. 8C), suggesting that adaptation of photosynthesis to a fluctuating condition may be limited by the inability to regulate pmf.

This study shows that differences may be observed under dynamic, fluctuating light between wild-type and mutant, with growth and photosynthetic efficiency severely inhibited in the mutant. More importantly, these results show that by imposing conditions that more closely simulate those found in nature, it is feasible to predict field outcomes for mutants or variants produced in the laboratory.

EXAMPLE 2

This example illustrates that use of continuous, in situ monitoring of whole plant properties compared to monitoring at discrete intervals. The continuous, in situ, monitoring detected a response that affected plant growth, and induced a transient, but useful, photosynthesis effect.

Arabidopsis thaliana plants (col-0) were grown on soil at 22° C. day temperature and 18° C. night temperature, 50% humidity and an intensity of μmol photons m$^{-2}$ s$^{-1}$ with an 16:8 day:night cycle. Chlorophyll a fluorescence images of steady state ($F_S$) and the fluorescence maximum at steady state ($F_M'$) were collected at growth light intensity and in the absence or presence of saturating illumination, respectively. These images were used to generate images of $\Phi_{II}$, a measure of photosynthetic efficiency on the day of and after treatment (by spraying) with 5 μM coronatine (cor) or water (control). Coronatine is a compound produced by a bacterial plant pathogen. As a chemical analog of jasmonic acid, it elicits a stress response, which includes differential induction and repression of classes of photosynthesis associated genes (PAGs). To determine if there were immediate and/or sustained effects on photosynthesis, imaging was performed discontinuously in an imager that used monochromatic (red) actinic light or continuously in situ in a growth chamber outfitted with a white actinic LED imaging system. For discontinuous imaging, plants were maintained in the growth chamber where they were treated and transferred to and from the fluorescence imager for measurements. For in situ imaging, the plants were allowed to readjust after transfer to the new chamber with white LED lighting for at least 24 hours prior to treatment and were kept in the chamber for the duration of experiment.

Discontinuous imaging revealed no differences between treated and untreated plants (FIG. 1). Furthermore the unusually low $\Phi_{II}$ values observed in control plants suggested that the stress of moving plants from the growth chamber to the imager may have masked any observable effect.

Figure 10:
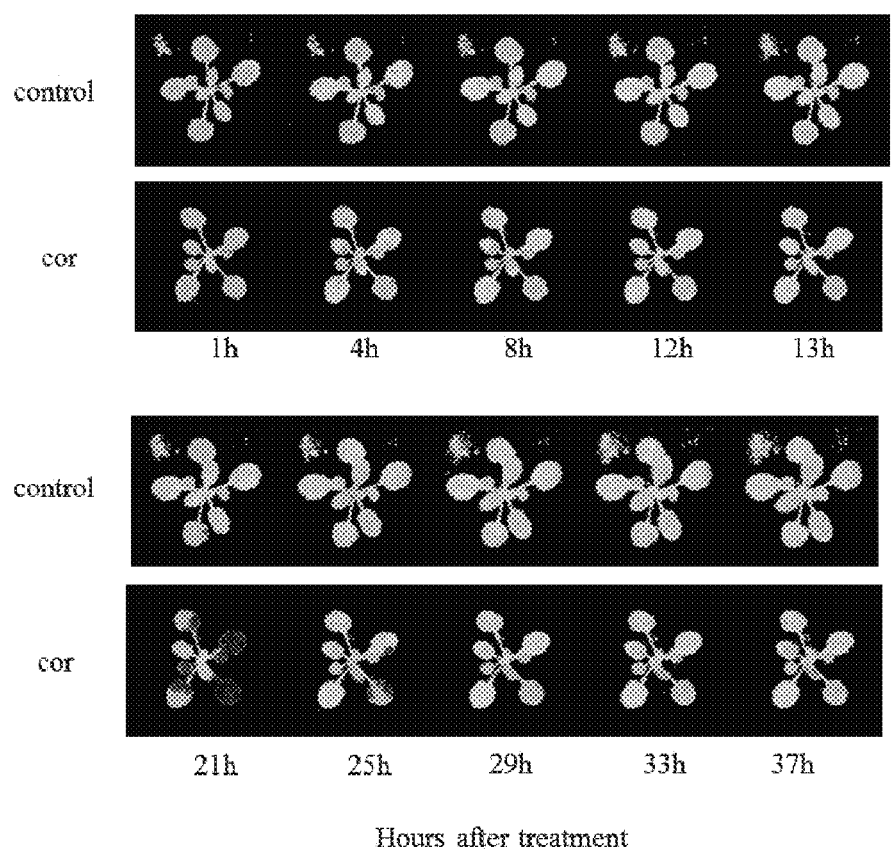
FIG. 10 shows images of ΦII generated from an imager that uses white actinic light for untreated (control) and coronatine-treated (cor) plants on the day of (upper panels) and day after (lower panels) treatment according to various embodiments. Darker (blue) areas correlate with lower ΦII values.

Imaging in situ with white LED actinic illumination minimized the stress of moving a plant from its growth environment to the instrument and with automated image capture facilitated collection of data at higher time resolution (FIG. 10). A large decrease in photosynthetic efficiency is observed early in the morning on the day after treatment (21 hours) but almost completely disappears by mid-morning (25 hours). The effect is also heterogeneous, more strongly observed in some leaves or not occurring at all in other (younger) leaves. In more recent studies (not shown), the effect was not observed on the second day after treatment.

By observing photosynthesis in situ, we have observed a transient effect on photosynthesis that has not be reported or observed before. Its transient nature implies that coronatine treatment (indirectly) delays the activation of photosynthesis by delaying: 1) activation of the Calvin-Benson-Bassham Cycle ($CO_2$ fixation), 2) stomatal reopening which limits $CO_2$ diffusion, 3) repriming of the $CO_2$ fixation from plastid starch 4) activation of sinks for fixed $CO_2$ (plastid starch formation, sucrose transport).

EXAMPLE 3

This example illustrates high-throughput analysis of photosynthetic properties using the disclosed system.

Figure 11A:
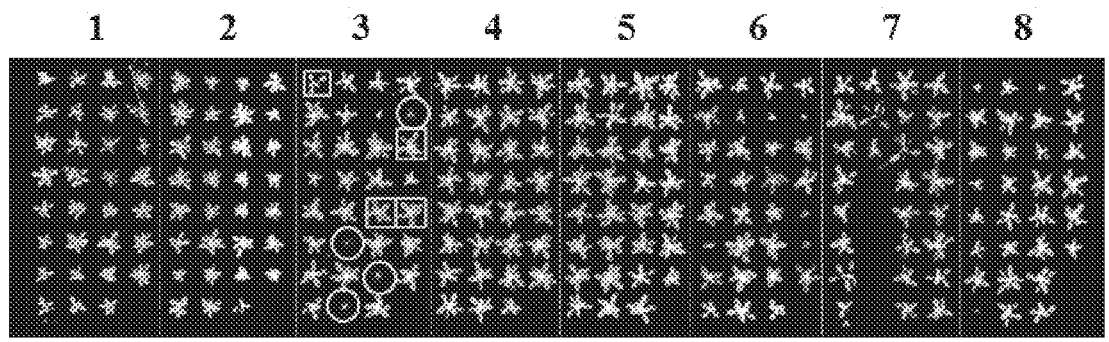
FIG. 11 (high throughput) shows ΦII (A) and qE (B) images for 8 minutes of illumination at 500 µmoles photons $m^{-2} sec^{-1}$ according to various embodiments. Mutant lines hprl (panel A, flat 3), SALK_110091 (panel B, flat 1) and rgsl-2 (Panel B, flat 6) are circled and the corresponding wild type controls (col-0) are boxed.
Figure 11B:
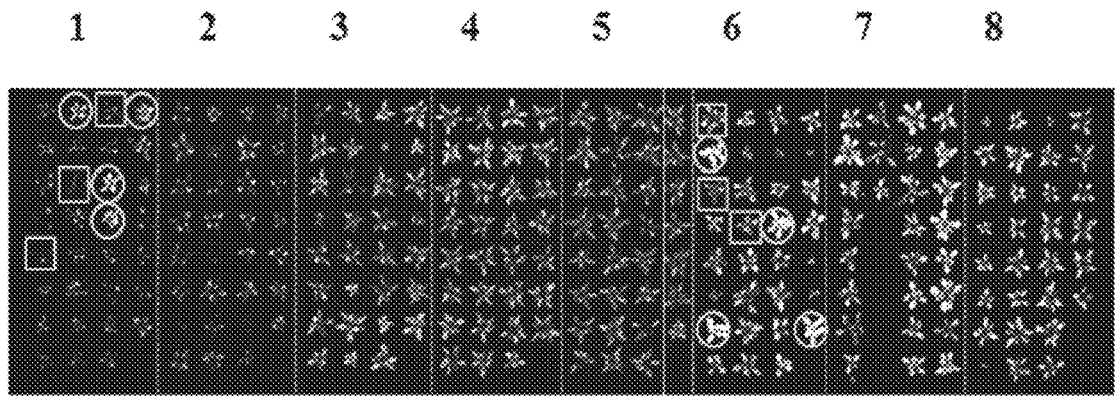

Approximately 50 mutant lines of Arabidopsis with corresponding wild type background lines were grown on soil at 20° C. and 50% humidity and under fluorescent lighting with intensity set at 100 μmoles photons m$^{-2}$ s$^{-1}$ for a 16 hr:8 hr day:night cycle. Each line was planted in triplicate or quadruplicate and grouped with other lines into one of eight flats. Plants within each flat were positioned randomly to test for reliability. Photosynthetic efficiency ($\Phi_{II}$) and energy dependent quenching ($q_E$) were monitored simultaneously for all 8 flats (using a 5 camera imaging system) during a 16 hour day with fluctuating light as described in Example 1 with actinic illumination provided by white LEDs. For 8 minutes of illumination at 500 μmoles photons m$^{-2}$ s$^{-1}$, three of the mutant lines clearly displayed photosynthetic phenotypes: 1) hprl, low $\Phi_{II}$, 2) SALK_110091, high $q_E$; and 3) rgsl-2, high qE (See FIG. 11). Ranges of photosynthetic behaviors are consistently seen, demonstrating the ability of the instrument to resolve high-resolution data from numerous plants.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the various embodiments described herein.

Although specific embodiments have been illustrated and described herein, it will be appreciated by those of ordinary skill in the art that any procedure that is calculated to achieve the same purpose may be substituted for the specific embodiments shown. This application is intended to cover any adaptations or variations of the present subject matter.

Therefore, it is manifestly intended that embodiments of this invention be limited only by the claims and the equivalents thereof.

What is claimed is:

1. A method of measuring a photosynthetic parameter comprising:
   illuminating a phototrophic organism with actinic illumination;
   switching off the actinic illumination for a period that minimizes perturbations to photosynthesis;
   pulsing the phototrophic organism with a measuring light during the period when the actinic illumination is switched off;
   collecting chlorophyll fluorescence data within the period when the actinic illumination is switched off; and
   determining a photosynthetic parameter from the fluorescence data.

2. The method of claim 1 wherein the actinic illumination comprises white spectrum in the range of about 380 nm to about 750 nm.

3. The method of claim 1 wherein the illuminating comprises light intensities in excess of about 2,500 micro moles photon $m^{-2}$ $s^{-1}$, at a distance of about 0.5 meters or greater.

4. The method of claim 1 wherein the actinic illumination is switched off for about 100 to about 120 microseconds.

5. The method of claim 1 wherein the pulsing is by a monochromatic light.

6. The method of claim 1 wherein the pulsing is light in the visible spectrum (400-700 nm).

7. The method of claim 1 wherein the pulsing is for about 1 to about 50 microseconds.

8. The method of claim 1 wherein the pulsing is a series of measuring pulses.

9. The method of claim 8 wherein the pulsing comprises from 1 to about 100 measuring pulses.

10. The method of claim 1 wherein the collecting is about 5 to about 50 microseconds within switching off the actinic illumination.

11. The method of claim 1 further comprising providing a saturating actinic flash with intensity in excess of about 20,000 micro moles $m^{-2}$ $s^{-1}$.

12. The method of claim 1 wherein the phototropic organism comprises whole plants, plant parts, tissue culture and/or cell suspensions.

13. The method of claim 1 wherein the chlorophyll fluorescence data is used to determine a physiological state of the phototrophic organism.

14. The method of claim 1 further comprises collecting and evaluating the data in response to environmental conditions selected from carbon dioxide, light intensity, light wavelength, light duration, water, nutrient content and combinations thereof.

15. The method of claim 1 wherein when the actinic illumination is switched off, the infrared spectral contamination of the chlorophyll fluorescence by the actinic illumination is minimized.

16. The method of claim 1 wherein the method is a continuous method of measuring multiple phototropic organisms.

17. The method of claim 1 wherein the measuring occurs over a period of days or weeks.

18. A system for measuring a photosynthetic parameter of a phototrophic organism comprising:
   an actinic light source and a measuring light source;
   a sensor for capturing chlorophyll fluorescent data on the phototrophic organism; and
   one or more processing units capable of switching the actinic and measuring light sources on and off in a manner which allows the phototrophic organism to be pulsed with the measuring light source during a period when the actinic light source is switched off, wherein the duration of the period when the actinic light source is switched off is short enough to minimize perturbations to photosynthesis.

19. The system of claim 18 adapted for use in a growth chamber or a green house.

20. The system of claim 18 wherein the actinic light is a white light emitting diode.

21. The system of claim 18 wherein the actinic light comprises light intensities in excess of about 2500 micro moles photon $m^{-2}$ $s^{-1}$, at a distance of about 0.5 meters or greater.

22. The system of claim 18 wherein the measuring light source is a monochromatic light.

23. The system of claim 18 further adapted to be portable.

24. The system of claim 18, wherein the period when the actinic light source is switched off is from about 100 microseconds to about 120 microseconds.

25. The system of claim 18 wherein the actinic light source is capable of providing a wavelength from about 380 to about 750 nm.

26. The system of claim 18 wherein the unit is capable of pulsing the measuring light source for about 1 to about 50 microseconds.

27. The system of claim 18 wherein the unit is capable of pulsing the measuring light source from 1 to about 100 times.

* * * * *